United States Patent [19]

White et al.

[11] 4,387,097
[45] Jun. 7, 1983

[54] MORPHOLINES

[75] Inventors: Alan C. White, Windsor; Gerald Bradley, Weybridge, both of England

[73] Assignee: John Wyeth and Brother Limited, Maidenhead, England

[21] Appl. No.: 357,023

[22] Filed: Mar. 11, 1982

[30] Foreign Application Priority Data

Mar. 27, 1981 [GB] United Kingdom ............. 8109713

[51] Int. Cl.³ .................. A61K 31/535; C07D 265/36
[52] U.S. Cl. .......................... 424/248.55; 424/248.58; 544/105
[58] Field of Search ............... 544/105; 424/248.55, 424/248.58

[56] References Cited

FOREIGN PATENT DOCUMENTS 2846567 5/1980 Fed. Rep. of Germany.

Primary Examiner—Richard Raymond
Attorney, Agent, or Firm—Richard K. Jackson

[57] ABSTRACT

Morpholine derivatives of the formula

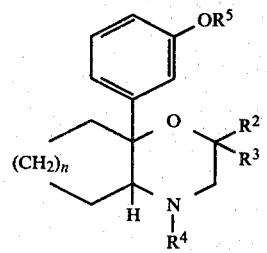

and their acid addition salts, wherein n represents 1, 2 or 3, $R^4$ is hydrogen, lower alkyl, lower alkenyl, lower alkynyl, aryl(lower)alkyl, 2-tetrahydrofurylmethyl or cyclo(lower)alkylmethyl, $R^2$ and $R^3$ are each hydrogen or alkyl of 1 to 10 carbon atoms and $OR^5$ is hydroxy, acyloxy or a protected hydroxy group possess analgesic and/or opiate antagonistic activity or are useful as intermediates for other compounds of formula I possessing such activity.

11 Claims, No Drawings

MORPHOLINES

This invention relates to morpholines, more particularly to 2,3-trimethylene-, tetramethylene- or pentamethylene-morpholines, to processes for their preparation and to pharmaceutical compositions containing them.

The present invention provides novel morpholine derivatives of the general formula (I)

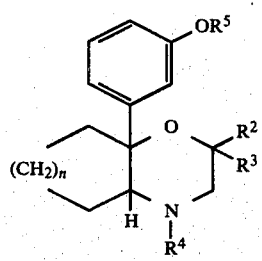

and their acid addition salts, particularly pharmaceutically acceptable acid addition salts. In this formula n represents 1,2 or 3, $R^4$ is hydrogen, lower alkyl, lower alkenyl, lower alkynyl, aryl(lower)alkyl, 2-tetrahydrofurylmethyl or cyclo(lower)alkylmethyl, $R^2$ and $R^3$ are each hydrogen or alkyl of 1 to 10 carbon atoms and $OR^5$ is hydroxy, acyloxy or a protected hydroxy group.

When $R^2$ and/or $R^3$ is an alkyl group it is preferably a lower alkyl group. The term "lower" as used herein means that the radical referred to contains 1 to 6 carbon atoms. The radical preferably contains 1 to 4 carbon atoms. For example when $R^2$, $R^3$ or $R^4$ is a lower alkyl radical, the radical may be, e.g. methyl, ethyl, propyl or butyl. When $R^4$ is lower alkenyl or lower alkynyl suitable groups include, for example, allyl, 2-methyl-2-propenyl, 3-methylbut-2-enyl and propynyl. When $R^4$ is aryl(lower)-alkyl the group can be, for example, benzyl or phenethyl (in which the phenyl ring may be substituted by one or more substituents such as lower alkyl, lower alkoxy, amino and halogen). When $R^4$ is cyclo(lower)alkylmethyl the group is preferably cyclopropylmethyl or cyclobutylmethyl. Preferably $R^4$ is lower alkyl. When $-OR^5$ is acyloxy the acyl group is preferably a lower alkanoyl group such as acetyl, propionyl or butyryl. When $-OR^5$ is protected hydroxy suitable groups include alkoxy (such as lower alkoxy e.g. methoxy, ethoxy, propyloxy, butyloxy particularly t-butyloxy), benzyloxy and (lower)alkoxymethoxy (e.g. methoxymethoxy) $OR^5$ is preferably hydroxy.

n is preferably 2 i.e. the preferred compounds of the invention are tetramethylenemorpholines (an alternative name for these being octahydro-2$\underline{H}$-1,4-benzoxazines) of the general formula

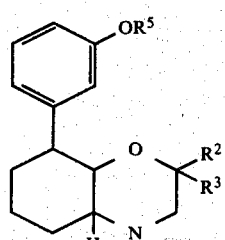

[where $R^2$, $R^3$, $R^4$ and $OR^5$ are as defined above] and their acid addition salts.

The compounds of the invention may be prepared by reduction of a lactam of general formula (II)

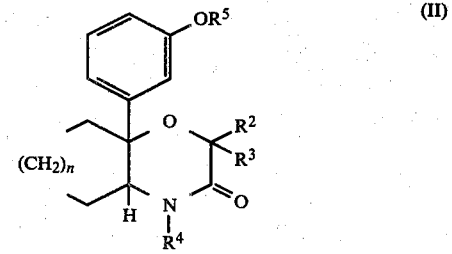

where n, $R^2$ and $R^3$ have the meanings given above and, if desired, converting a free base of general formula (I) into an acid addition salt thereof. The reduction may be carried out by, for example, a hydride transfer agent (e.g. lithium aluminium hydride). In certain instances more than one reducing agent may be required. For example reduction of a compound of general formula (II) in which at least one of $R^2$ and $R^3$ is hydrogen with lithium aluminium hydride can give some product containing a double bond in the 2,3-position of the oxazine ring and this compound may be then reduced by catalytic hydrogenation.

Once a compound of general formula (I) has been prepared it may be converted into another compound of general formula (I) by methods known per se. For example, a compound in which $R^4$ is lower alkyl, lower alkenyl, lower alkynyl, aryl(lower)alkyl, 2-tetrahydrofurylmethyl or cycloalkylmethyl may be prepared by "N-alkylating" a compound in which $R^4$ is hydrogen. By "N-alkylating" is meant introducing on to the nitrogen atom of the morpholine ring a lower alkyl, lower alkenyl, lower alkynyl, aryl(lower)alkyl, 2-tetrahydrofurylmethyl or cycloalkylmethyl radical. In one method of carrying out the "N-alkylating" process a compound of general formula I in which $R^4$ is hydrogen is reacted with a halide of general formula $R^{4'}$—Hal where $R^{4'}$ is lower alkyl, lower alkenyl, lower alkynyl, aryl(lower)alkyl, 2-tetrahydrofurylmethyl or cyclo(lower)alkylmethyl (or, is reacted with for example, a corresponding tosylate or mesylate) in the presence of an acid acceptor such as alkali metal carbonate (e.g. potassium carbonate), preferably in solution in an organic solvent.

Alternatively the compound of general formula (I) in which $R^4$ is hydrogen may be alkylated by reductive alkylation i.e. by treatment with an aldehyde and hydrogen in presence of a hydrogenation catalyst. A preferred method of cycloalkyl-methylating involves reacting the N-unsubstituted compound with a cycloalkylcarbonyl chloride to give an intermediate N-carbonyl compound which may be reduced with, for example, a hydride transfer agent.

A compound of general formula (I) in which $OR^5$ is hydroxy can be obtained by removing the protecting group from a compound in which $OR^5$ is a protected hydroxy group. For example the ether group in a compound in which $R^5$ is lower alkyl, lower alkoxymethyl or benzyl may be removed in known manner, e.g. by treating the lower alkyl or benzyl ether with hydrogen bromide or boron tribromide, by treating the lower alkyl ether with diisobutylaluminium hydride or by subjecting the benzyl ether to hydrogenolysis or by treating the (lower) alkoxymethyl or t-butyl ether with dilute acid. Similarly a compound of general formula (I) in which $R^4$ is benzyl may be hydrogenolysed to a compound of general formula (I) in which $R^4$ is hydrogen which, if desired may then be "alkylated" as hereinbefore described. Compounds in which $R^4$ is lower alkyl, particularly methyl may also be dealkylated to compounds in which $R^4$ is hydrogen, e.g. by reaction with ethyl-, phenyl-, vinyl- or 2,2,2-trichloroethyl-chloroformate followed by removal of the resulting N-substituent with, for example, dilute acid or zinc and acetic acid or basic conditions as appropriate.

A compound of general formula (I) in which $OR^5$ is hydroxy can be acylated (e.g. with acetic anhydride) to give a corresponding compound in which $OR^5$ is an acyloxy group such as a lower alkanoyloxy radical.

Two or more of the above mentioned processes for interconverting the compounds of general formula (I) may, if desired, be carried out consecutively. In some instances it may be necessary to protect one or more of the functional groups on the molecule while reaction occurs at another functional group and then subsequently remove the protecting group or groups.

Lactams of general formula (II) may be prepared by cyclisation of an amide of general formula

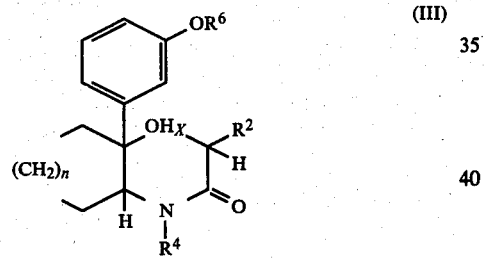

(III)

where n, $R^2$ and $R^4$ are as defined above, X is bromo or chloro, and $-OR^6$ is a protected hydroxy group and, if required, alkylating the product. The cyclisation may be carried out with a basic agent such as an alkali metal hydride or alkali metal hydroxide. Where a lactam of formula (II) is desired in which $R^3$ is alkyl the corresponding lactam in which $R^3$ is hydrogen may be alkylated. The alkylation may be carried out, for example, with an alkyl halide in presence of a strong base such as sodamide, lithium diisopropylamide, lithium tetramethylpiperidide, bromomagnesium diisopropylamide or N-tertiarybutylcyclohexylamide.

If desired, the $-OR^5$ protected hydroxy group in the lactam of formula (II) may be deprotected to give a lactam where $-OR^5$ is hydroxy. In this case the protecting group and the method of deprotection are chosen, for example, from those mentioned hereinabove, so that the product is stable under the chosen conditions.

The amides of formula (III) are preferably prepared by condensing an α-halo acid halide of general formula (IV)

with an amino alcohol of general formula

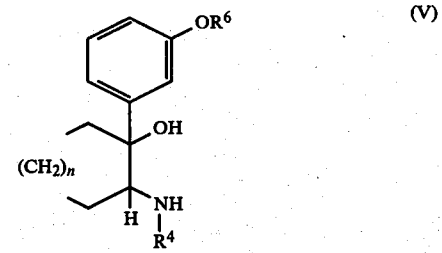

In general formula (IV) and (V) n,$R^2$,$R^4$,$OR^6$ and X have the meanings given above and $X^1$ is chloro or bromo. The condensation can be carried out in presence of a basic condensing agent, e.g. triethylamine.

The α-halo acid halide of general formula (IV) and the amino alcohol of general formula (V) are known compounds or can be prepared by methods known for analogous compounds. For example, the choice of method used to prepare the amino alcohol will depend upon the stereochemistry required in the final product. For example aminoalcohols which are useful as intermediates for preparing final compounds (I) possessing a trans ring fusion may be prepared by the method illustrated below

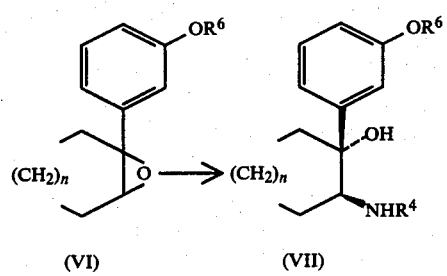

(VI)                (VII)

The oxiran of formula (VI) is reacted with an amine of formula $R_4NH_2$ to give the amino alcohol of formula (VII).

The aminoalcohols which are useful as intermediates for preparing final compounds (I) possessing a cis ring fusion may be prepared by the method illustrated below:

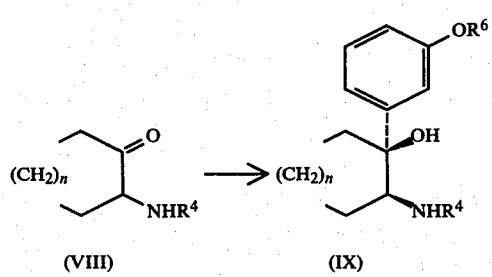

(VIII)               (IX)

The compound of formula (VIII) may be reacted with a m-(protected hydroxy) phenyl Grignard reagent to give the compound of formula (IX).

If in any of the processes described above the compound of the invention is obtained as an acid addition salt, the free base can be obtained by basifying a solution of the acid addition salt. Conversely, if the product of the process is a free base a pharmaceutically acceptable acid addition salt may be obtained by dissolving the free base in a suitable organic solvent and treating the solution with an acid, in accordance with the conventional procedures for preparing acid addition salts from base compounds.

Examples of acid addition salts are those formed from inorganic and organic acids, such as sulphuric, hydrochloric, hydrobromic, phosphoric, tartaric, fumaric, oxalic, maleic, citric, acetic, formic, methane-sulphonic and p-toluenesulphonic acids.

The compounds of the invention contain at least three asymmetric carbon atoms and hence can exist in more than one isomeric form. For example the substituents

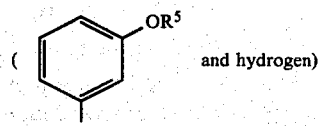 and hydrogen)

at the bridgehead carbon atoms may be cis or trans to each other and also the

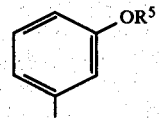

substituent may be cis or trans to the $R^2$ substituent. The various isomeric forms can be obtained or separated by standard procedures. For example, as exemplified above, by suitable choice of starting materials products can be obtained with the desired configuration. The products will normally be obtained as racemates of the d- and l-enantiomorphs but optical isomers may be prepared by resolving a racemic mixture by standard methods described in the literature. The racemate may be prepared by any of the processes outlined above. It is to be understood that the resolution may be carried out on the racemic mixture of the final desired product or it may be carried out on a racemic precursor of the desired compound provided further chemical transformations do not cause racemisation.

The compounds of the invention in which $OR^5$ is a protected hydroxy group such as lower alkoxy are useful, as mentioned above, for preparing compounds in which $OR^5$ is hydroxy. The compounds of general formula (I) in which $OR^5$ is hydroxy or acyloxy and their pharmaceutically acceptable acid addition salts possess analgesic activity and/or opiate antagonistic activity. Some compounds also possess hypotensive or antihypertensive activity. In a standard test for analgesic activity in which the compound is assessed for its ability to inhibit phenylbenzoquinone-induced writhing in mice (based upon the method of E. Siegmund et al., Proc. Soc. exp. Biol. Med., 1957, 95, 729–731) 3-[(2R*,4aR*,8aS*)-octahydro-2,4-dimethyl-2H-benzoxazin-8a-yl]phenol and (2R*,4aR*,8aS*)-3-(2-ethyloctahydro-4-methyl-2H-1,4-benzoxazin-8a-yl)-phenol, representative compounds of the invention, exhibited $ED_{50}$'s of respectively 0.3 and 2.7 mg/kg (subcutaneous). In a standard test for opiate antagonism based upon the antagonism of morphine-induced Straub tail in mice (Aceto et al., Brit. J. Pharmac., 1969, 36, 225–239), 3-[(2R*,4aR*,8aS*)-octahydro-2,4-dimethyl-2H-benzoxazin-8a-yl]phenol and (2R*,4aS*,8aS*)-3-(2-ethyloctahydro-4-methyl-2H-1,4-benzoxazin-8a-yl)phenol, representative compounds of the invention, exhibited $ED_{50}$'s of respectively 1.7 and 0.13 mg/kg (subcutaneous).

The invention provides a pharmaceutical composition comprising a compound of general formula (I) in which $OR^5$ is hydroxy or acyloxy or a pharmaceutically acceptable acid addition salt thereof in association with a pharmaceutically acceptable carrier. Any suitable carrier known in the art can be used to prepare the pharmaceutical compositions. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders or tablet-disintegrating agents; it can also be an encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10–80% of the active ingredient. Suitable solid carriers are magnesium carbonate, magnesium stearate, talc, lactose, pectin, dextrin, starch, gelatin, tragacanth, methylcellulose, sodium carboxymethyl cellulose, a low melting wax, and cocoa butter. The term "composition" is intended to include the formulation of an active ingredient with encapsulating material as carrier to give a capsule in which the active ingredient (with or without other carriers) is surrounded by the carrier, which is thus in association with it. Similarly cachets are included.

Sterile liquid form compositions include sterile solutions, suspensions, emulsions, syrups and elixirs. The active ingredients can be dissolved or suspended in a pharmaceutically acceptable sterile liquid carrier, such as sterile water, sterile organic solvent or a mixture of both. Preferably a liquid carrier is one suitable for parenteral injection. Where the active ingredient is sufficiently soluble it can be dissolved in normal saline as a carrier; if it is too insoluble for this it can often be dissolved in a suitable organic solvent, for instance aqueous propylene glycol or polyethylene glycol solutions. Aqueous propylene glycol containing from 10 to 75% of the glycol by weight is generally suitable. In other instances other compositions can be made by dispersing the finely-divided active ingredient in aqueous starch or sodium carboxymethyl cellulose solution, or in a suitable oil, for instance arachis oil. Liquid pharmaceutical compositions which are sterile solutions or suspensions can be utilised by intra-muscular, intraperitoneal or subcutaneous injection. In many instances a compound is orally active and can be administered orally either in liquid or solid composition form.

Preferably the pharmaceutical composition is in unit dosage form, e.g. as tablets or capsules. In such form, the composition is sub-divided in unit doses containing appropriate quantities of the active ingredients; the unit dosage forms can be packaged compositions, for example packeted powders or vials or ampoules. The unit dosage form can be a capsule, cachet or tablet itself, or it can be the appropriate number of any of these in package form. The quantity of the active ingredient in a unit dose of composition may be varied or adjusted from 5 mg. or less to 500 mg. or more, according to the particular need and the activity of the active ingredient. The invention also includes the compounds in the absence of the carrier where the compounds are in unit dosage form. The following Examples illustrate the invention.

EXAMPLE 1

(1R*,2S*)-1-(3-Methoxyphenyl)-2-methylamino-1-cyclohexanol (a) Crude 1-(3-methoxyphenyl)cyclohexene (prepared by the method of F. Macchia et al., Tetrahedron, 1973, 29, 2183-8) (8.35 g) was dissolved in dichloromethane (50 cm$^3$) and treated dropwise, with stirring and external cooling to maintain the internal temperature at 15°–20°, with m-chloroperoxybenzoic acid (10 g) in dichloromethane (150 cm$^3$) over ¾ hr. The mixture was then stirred at room temperature for 1 hr. Excess peracid was destroyed by addition of 10% sodium sulphite. The mixture was washed with half-saturated sodium bicarbonate solution (2×50 cm$^3$) until all solid m-chlorobenzoic acid had dissolved, and then with water and saturated brine. The organic phase was then evaporated, leaving crude 1-(3-methoxyphenyl)-cyclohexane-1,2-oxide as a yellow oil (10.6 g)

(b) The crude epoxide from part (a) (10.3 g) was dissolved in ethanolic methylamine (33%; 125 cm$^3$) and heated in a sealed vessel at 100°–110° for 24 hrs. The mixture was evaporated under reduced pressure and the dark, oily residue was dissolved in ether (50 cm$^3$). The solution was extracted with 2 N sulphuric acid (3×25 cm$^3$). The combined acid extracts were back-extracted with ether (3×20 cm$^3$) and the ether solutions were discarded. The acid phase was made basic with potassium carbonate and the product was extracted into dichloromethane. The combined extracts were dried (NaSO$_4$) and evaporated, giving a light brown solid (8.90 g). Recrystallisation from cyclohexane gave the title compound as colourless crystals (4.99 g) m.p. 113°–4°.

Found: C, 71.6; H, 9.1; N, 5.6 C$_{14}$H$_{21}$NO$_2$ requires C, 71.45; H, 9.0; N, 5.95%.

EXAMPLE 2

(1R*,2S*)-2-(2-bromopropion-N-methylamido)-1-(3-methoxyphenyl)-1-cyclohexanol

The product of Example 1 (3.525 g) in dichloromethane (55 cm$^3$) containing triethylamine (2.1 cm$^3$, 1.525 g) was treated, with stirring and external cooling to maintain the internal temperature at 20°, with 2-bromopropionyl bromide (3.24 g) in dichloromethane (25 cm$^3$) over 1 hr. The mixture was kept at room temperature for a further 2 hr. and was then concentrated under reduced pressure to an oily solid. The solid was partitioned between water (30 cm$^3$) and ether (30 cm$^3$). The ether phase was washed with N sulphuric acid (30 cm$^3$), saturated brine (30 cm$^3$), dried (Na$_2$SO$_4$) and evaporated, leaving crude title compound as a pale green oil (5.99 g) characterised spectroscopically.

EXAMPLE 3

(2R*,4aR*,8aS*) and (2R*,4aS*,8aR*-Hexahydro-8a-(3-methoxyphenyl)-2,4-dimethyl-2H-1,4-benzoxazin-3(4H)-one Crude bromoamide product of Example 2 (5.45 g), was treated at room temperature in propan-2-ol (50 cm$^3$) with 10 N aqueous sodium hydroxide (4.5 cm$^3$) with stirring for 19 hr. The solvent was removed under reduced pressure and the aqueous residue was diluted with water (30 cm$^3$) and extracted with ether (3×50 cm$^3$). The combined extracts were dried (Na$_2$SO$_4$), evaporated and re-evaporated with toluene (50 cm$^3$) to remove residual propan-2-ol and water, leaving crude title compound as a pale green oil (4.53 g).

EXAMPLE 4

(2R*,4aR*,8aS*)-Octahydro-8a-(3-methoxyphenyl)-2,4-dimethyl-2H-1,4-benzoxazine (a) Direct reduction A suspension of lithium aluminium hydride (2.1 g) in dry ether (50 cm$^3$) was treated over 2 hr with a solution of crude lactam product of Example 3 (7.65 g) in dry ether (100 cm$^3$). The mixture was heated to reflux for 24 hr, cooled, and treated with saturated potassium sodium tartrate solution (300 cm$^3$). The phases were separated and the aqueous phase was extracted with ether (3×50 cm$^3$). The combined ether solutions were dried (Na$_2$SO$_4$) and evaporated, leaving impure title compound base as a pale yellow oil (6.97 g).

The crude base (6.71 g) was converted to its hydrogen oxalate salt in ethyl acetate, and recrystallised from ethyl acetate-methanol (charcoal). The crystals were collected and washed with ethyl acetate (2×25 cm$^3$), then ether (25 cm$^3$) and dried, giving the title compound hydrogen oxalate as colourless crystals (4.65 g) m.p. 204°–6° (decomp. with gas evolution).

Found: C, 62.4; H, 7.8; N, 3.7. C$_{17}$H$_{25}$NO$_2$.C$_2$H$_2$O$_4$ requires C, 62.45; H, 7.45; N, 3.8%.

(b) Alternative process

Crude lactam product of Example 3 (4.26 g) in ether (100 cm$^3$) was treated with solid lithium aluminium hydride (0.56 g), at room temperature. The mixture was heated to reflux for 3 hr and then kept at room temperature overnight (22 hr.). Saturated potassium sodium tartrate solution (50 cm$^3$) was added, stirred 1 hr, and the phases were separated. The aqueous phase was extracted with ether (3×30 cm$^3$). The extracts were dried (Na$_2$SO$_4$) and evaporated, leaving impure (4aR*,8aS*)-4a,5,6,7,8,8a-hexahydro-8a-(3-methoxyphenyl)-2,4-dimethyl-4H-benzoxazine as a colourless oil (3.5 g) which rapidly turned yellow-brown on exposure to air.

The impure product (1.0243 g) was hydrogenated in ethanol (30 cm$^3$) over 5% Pd/C (100 mg) at atmospheric pressure and 15°–16°. Total absorption 75 cm$^3$ (3.07 mmol, 82%) after 280 min. The catalyst was removed, washed with ethanol, and the filtrate and washings were evaporated under reduced pressure, leaving a yellow oil (1.07 g).

The oil was chromatographed over silica gel to give the title compound as a colourless oil (0.75 g) shown spectroscopically and by mixed melting point of the oxalate salts to be identical to material prepared by the direct route (a).

EXAMPLE 5

3-[(2R*,4aR*,8aS*)-octahydro-2,4-dimethyl-2H-benzoxazin-8a-yl]phenol (2R*,4aR*,8aS*)-Octahydro-8a-(3-methoxyphenyl)-2,4-dimethyl-2H-1,4-benzoxazine hydrogen oxalate (1 g) was slurried in dry toluene (10 cm$^3$) under dry nitrogen. Diisobutylaluminium hydride (20% in toluene, 1.2 M, 18.5 cm$^3$) was added cautiously and the mixture was then heated to reflux for 22 h. The cooled mixture was treated very cautiously with saturated Rochelle salt solution (100 cm$^3$), followed by ether (50 cm$^3$). The mixture was stirred to dissolve aluminium salts and the phases were then separated. The aqueous phase was extracted repeatedly with ether (8×30 cm$^3$) and then with chloroform (50 cm$^3$). The organic phases were combined, dried (Na$_2$SO$_4$) and evaporated, giving impure product as an oil which rapidly crystallised (0.87 g). The solid was converted to its hydrochloride salt and crystallised from ethanol-methanol giving the title compound hydrochloride as colourless crystals (0.47 g) m.p. 285°-8° (decomp. above 270°).

Found: C, 64.6; H, 8.1; N, 4.55. C$_{16}$H$_{23}$NO$_2$.HCl requires C, 64.5; H, 8.1; N, 4.7%.

EXAMPLE 6

(1R*,2R*)-1-(3-Methoxyphenyl)-2-methylaminocyclohexanol and (1R*,2S*)-1-(3-methoxyphenyl)-2-methylaminocyclohexanol 2-Methylaminocyclohexanone hydrochloride (L. Bernardi, C. Fuganti, and D. Ghiringhelli, Gazz. Chim. Ital. 1968, 98, 836-847) (20 g) was added slowly in small portions to a stirred refluxing solution of 3-methoxyphenyl magnesium bromide [prepared from magnesium (16 g) and 3-bromoanisole (120 g)] in dry ether (350 cm$^3$) and T.H.F. (200 cm$^3$). The mixture was heated under reflux for 17 hr. and was then cooled and poured on to ice (330 g) containing concentrated hydrochloric acid (60 cm$^3$). The phases were separated and the ether phase was extracted with 2 N-hydrochloric acid (50 cm$^3$). The combined acid solutions were extracted with ether (100 cm$^3$) and were then concentrated under reduced pressure to remove T.H.F. The residual aqueous solution was made alkaline with concentrated ammonia and the product was extracted into ether (5×250 cm$^3$). The combined, dried (Na$_2$SO$_4$) extracts were evaporated leaving an oil, which was re-evaporated with toluene (50 cm$^3$) to give the impure amino alcohol mixture as a yellow oil (27.55 g). On standing the oil became partially crystalline and was separated by filtration into a liquid phase (18.03 g) and a pasty solid (8.52 g). The pasty solid was shown by IR, NMR and GLC to consist largely of the (1R*,2S*) isomer, with the (1R*,2R*) isomer as minor component. The liquid phase was shown, by IR, NMR and GLC to consist of ~85% (1R*,2R*) isomer, no detectable (1R*,2S*) isomer, and 10-15% of 1-(3-methoxyphenyl)-2-methylaminocyclohexene. The 1R*,2R* isomer was converted to its hydrochloride and recrystallised from ethyl acetate-methanol giving the title compound hydrochloride as colourless prisms, m.p. 217°-220° C.

Found: C, 61.6; H, 8.3; N, 4.9. C$_{14}$H$_{21}$NO$_2$.HCl requires C, 61.9; H, 8.2; N, 5.15%.

EXAMPLE 7

(2R*,4aR*,8aR*) and (2R*,4aS*,8aS*)-hexahydro-8a-(3-methoxyphenyl)-2,4-dimethyl-2H-1,4-benzoxazin-3(4H)-one Crude (1R*,2R*)-1-(3-methoxyphenyl)-2-methylaminocyclohexanol (4.7 g, from Example 6) was dissolved in dichloromethane (50 cm$^3$) containing triethylamine (2.8 cm$^3$, 2.02 g). The solution was cooled to 10° in a bath of cold water and treated dropwise with 2-bromopropionyl bromide (2.33 cm$^3$, 4.32 g). The mixture was stirred for 1 hr. while cooling and was then concentrated under reduced pressure to an oily solid. This was partitioned between N hydrochloric acid (50 cm$^3$) and ether (50 cm$^3$), and the aqueous phase was extracted with further ether (3×20 cm$^3$). The ether extracts were dried (Na$_2$SO$_4$) and evaporated, leaving crude (1R*,2R*)-2-(2-bromopropionyl-N-methylamino)-1-(3-methoxyphenyl)cyclohexanol as a yellow oil (7.7 g).

The crude, oily bromoamide (7.7 g) was dissolved in warm propan-2-ol (50 cm$^3$) and treated with vigorous stirring with 10 N aqueous sodium hydroxide (4 cm$^3$). The mixture was kept at room temperature overnight and was then concentrated under reduced pressure. The residue was re-evaporated with toluene (50 cm$^3$) to remove propan-2-ol, and the residue was diluted with water (50 cm$^3$). The product was extracted into ether (4×25 cm$^3$) and the extracts were dried (Na$_2$SO$_4$) and evaporated, leaving a crude mixture of the title diastereoisomers as a brown oil (5.42 g).

EXAMPLE 8

(2R*,4aR*,8aR*) and (2R*,4aS*,8aS*)-octahydro-8a-(3-methoxyphenyl)-2,4-dimethyl-2H-1,4-benzoxazines Lithium aluminium hydride (1.8 g) was stirred and heated to reflux in dry ether (50 cm$^3$) for 5 min. before the slow addition of the mixture of (2R*,4aR*,8aR*) and (2R*,4aS*,8aS*) lactam products of Example 7 (5.42 g) in dry ether (100 cm$^3$) over 30 min. The mixture was heated to reflux for 4 hr. and was then cooled and treated with saturated Rochelle salt solution (100 cm$^3$) and water (25 cm$^3$). The phases were separated and the aqueous phase was extracted with further ether. The combined ether phases were dried (Na$_2$SO$_4$) and evaporated, leaving a crude mixture of the title benzoxazines as an oil (4.47 g). The mixture was separated by chromatography over silica gel giving the title compound (2R*,4aR*,8aR*) isomer (2.53 g) which crystallised on standing and the title compound (2R*,4aS*8aS*) isomer (1.63 g) as an oil.

EXAMPLE 9

(4aR*,8aS*)-Hexahydro-8a-(3-methoxyphenyl)-4-methyl-2H-1,4-benzoxazin-3(3H)-one The product of Example 1 (4.7 g) in dichloromethane (60 cm$^3$) containing triethylamine (2.8 cm$^3$), was treated with chloroacetyl chloride (1.6 cm$^3$) dropwise with stirring and external cooling. The mixture was stirred for a further ¾ hr. and was then evaporated. The residue was dissolved in 2 N sulphuric acid (30 cm$^3$) and the neutral product was extracted into ether. The ether extracts were washed with 2 N sulphuric acid, water and saturated brine and dried (Na$_2$SO$_4$). Removal of the solvent left crude (1R*,2R*)-2-(2-chloroacetyl-N- methylamino)-1-(3-methoxyphenyl)cyclohexanol as an oil (6.44 g).

The crude amide (6.03 g) was dissolved in warm propan-2-ol (60 cm$^3$) and treated with 10 N sodium hydroxide solution (5.8 cm$^3$). The mixture was stirred vigorously at room temperature for 1 hr. The solvent was removed and the aqueous residue was diluted with water (30 cm$^3$). The cyclised product was extracted into ether and the combined extracts were washed with saturated brine and dried (Na$_2$SO$_4$). Removal of the solvent left crude title product as an oil (5.26 g).

EXAMPLE 10

(2R*,4aS*,8aR*)-Hexahydro-8a-(3-methoxyphenyl)-2,4-dimethyl-2H-1,4-benzoxazin-3(4H)-one A solution of crude (4aR*,8aS*)-hexahydro-8a-(3-methoxyphenyl)-4-methyl-2H-benzoxazin-3(4H)-one (1.63 g) in dry THF (5 cm$^3$) was added dropwise under nitrogen to a stirred solution of lithium di-isopropylamide [from n-butyllithium 1.55 M in hexane (3.75 cm$^3$) and di-isopropylamine (0.82 cm$^3$, 0.59 g) in THF (2 cm$^3$)] at 10°. The mixture was stirred for 15 mins at 10° and was then treated with methyl iodide (1 cm$^3$, 2.28 g). Stirring was continued for a further 15 min, then the mixture was poured into 0.5 N hydrochloric acid (25 cm$^3$) and concentrated under reduced pressure to remove THF and excess methyl iodide. The product was then extracted into ether and the extracts were dried (Na$_2$SO$_4$) and evaporated, leaving a yellow gum (1.63 g) shown by IR, NMR and GLC to contain ~85% title compound, and about 5% of the (2R*,4aR*,8aS*) isomer.

EXAMPLE 11

(2R*,4aR*,8aS*)-2-Ethyl-hexahydro-8a-(3-methoxyphenyl)-4-methyl-2H-1,4-benzoxazin-3(4H)-one The product of Example 1 (2.35 g) in dichloromethane (25 cm$^3$) containing triethylamine (1.4 cm$^3$) was treated dropwise with 2-bromobutyryl chloride (1.2 cm$^3$). The mixture was then allowed to cool to room temperature over 2½ hr. The solvent was removed and the semi-solid residue was partitioned between ether (50 cm$^3$) and N hydrochloric acid (50 cm$^3$). The aqueous phase was extracted with further ether and the combined ether extracts were dried (Na$_2$SO$_4$) and evaporated, leaving the bromo-amide as an oil (3.73 g).

The crude bromo-amide (3.65 g) in warm propan-2-ol (30 cm$^3$) was treated with 10 N sodium hydroxide solution (3 cm$^3$) with vigorous stirring for 3 hr. The solvent was removed and the aqueous residue was diluted with water (30 cm$^3$). The product was extracted into ether, dried (Na$_2$SO$_4$), and the solvent removed, leaving the crude title compound as an oil (2.55 g).

EXAMPLE 12

(2R*,4aR*,8aR*)-3-(Octahydro-2,4-dimethyl-2H-1,4-benzoxazin-8a-yl)phenol

The (2R*,4aR*,8aR*) product of Example 8 (2.24 g) in dry toluene (22 cm$^3$) was treated under argon at room temperature with di-isobutylaluminium hydride (25° wt % in toluene, 11 cm$^3$) and the mixture was then heated to reflux for 22 hr. The cooled solution was treated with saturated potassium sodium tartrate solution (25 cm$^3$), ether (20 cm$^3$), and water (10 cm$^3$) and stirred until the aluminium salts had dissolved. The mixture was separated. The aqueous phase was extracted with ether and the combined organic solutions were dried (Na$_2$SO$_4$) and evaporated, leaving the phenol as a solid (2.11 g), m.p. 188°–193°. The solid was converted to its hydrochloride salt in ethyl acetate-ether and the salt was recrystallised from ethyl acetate-methanol, giving the title compound hydrochloride as colourless crystals (2.17 g), m.p. 246°–8° (decomp. rapidly above 200°).

Found: C, 64.6; H, 8.4; N, 4.5. C$_{16}$H$_{23}$NO$_2$.HCl requires C, 64.5; H, 8.1; N, 4.7%.

EXAMPLE 13

(2R*,4aS*,8aS*)-3-(Octahydro-2,4-dimethyl-2H-1,4-benzoxazin-8a-yl)phenol

The (2R*,4aS*,8aS*) product of Example 8 (1.4 g) in toluene (15 cm$^3$) was treated under argon at room temperature with di-isobutylaluminium hydride (25 wt % in toluene, 6.7 cm$^3$) and the mixture was heated to reflux for 22 hr. The cooled solution was treated cautiously with saturated potassium sodium tartrate solution (25 cm$^3$), ether (20 cm$^3$) and water (10 cm$^3$) and stirred until aluminium salts had dissolved. The mixture was separated. The aqueous phase was extracted with ether and the combined organic solutions were dried (Na$_2$SO$_4$) and evaporated, leaving the phenol as a colourless oil (1.46 g). The oil was converted to its hydrochloride salt in ethyl acetate-ether and the salt was crystallised from ethyl acetate-methanol giving the title compound hydrochloride as colourless crystals (1.2 g), m.p. 246°–8° (decomp. rapidly above 200°).

Found: C, 64.4; H, 8.3; N, 4.3. C$_{16}$H$_{23}$NO$_2$.HCl requires: C, 64.5; H, 8.1; N, 4.7%.

EXAMPLE 14

(4aR*,8aS*)-Octahydro-8a-(3-methoxyphenyl)-4-methyl-2H-1,4-benzoxazine (a) using lithium aluminium hydride The crude product of Example 9 (1.02 g) in dry ether (50 cm$^3$) was added dropwise over ¾ hr. to a refluxing suspension of lithium aluminium hydride (0.35 g) in dry ether (25 cm$^3$). After 6 hr. at reflux, the mixture was cooled and treated dropwise with saturated Rochelle salt solution (100 cm$^3$) and the mixture was stirred until the solids had dissolved. The phases were separated and the aqueous phase was extracted with ether. The combined organic solutions were dried (Na$_2$SO$_4$) and evaporated, leaving crude title compound as a clear oil (0.93 g).

(b) using borane-T.H.F. complex

The crude product of Example 9 (1.02 g) in dry T.H.F. (10 cm$^3$) was treated at room temperature under nitrogen with borane-T.H.F. complex (1 M in T.H.F., 10 cm$^3$). The mixture was kept at room temperature for 24 hr. under nitrogen, and was then added to a stirred mixture of hydrogen peroxide (20 vol, ~6% w/v, 25 cm$^3$) and 2 N sodium hydroxide (5 cm$^3$). After ½ hr. sodium sulphite was added until no peroxide was detected by starch-iodide paper, and the phases were separated. The aqueous phase was extracted with ether and the combined organic phases were dried (Na$_2$SO$_4$) and evaporated. The residue was re-evaporated with toluene (50 cm$^3$). The almost colourless oily borane adduct (1.1 g) was kept in an open flask for 4 weeks to hydrolyse with atmospheric moisture, giving an opaque, solid mass. The mass was partitioned between N sodium hydroxide (15 cm$^3$) and ether (15 cm$^3$) and the aqueous phase was extracted with further ether. The ether phases were dried (NaSO4) and evaporated, giving the title compound as a clear, colourless oil (0.74 g).

EXAMPLE 15

(4aR*,8aS*)-3-(Octahydro-4-methyl-2H-1,4-benzoxazin-8a-yl)phenol

The crude product of Example 14 (1.34 g) in dry toluene (20 cm$^3$) was treated at room temperature under nitrogen with di-isobutylaluminium hydride (1.2 M in toluene, 8.6 cm$^3$). The solution was then heated to reflux for 22 hr. The cooled solution was treated with saturated Rochelle salt solution (50 cm$^3$), then water (12.5 cm$^3$) and ether (15 cm$^3$). The resulting suspension was stirred until the aluminium salts had dissolved. The mixture was separated. The aqueous phase was extracted with chloroform (4×30 cm$^3$) and the combined organic phases were dried (Na$_2$SO$_4$) and evaporated, leaving a pink solid (1.16 g). This was converted to its hydrochloride salt in ethyl acetate-methanol-ether and the solid product was washed with ether giving a crystalline solid (0.69 g) of the title compound as the hydrochloride two thirds hydrate, m.p. 250°-2° (decomp.).

Found: C, 60.9; H, 7.8; N, 4.5. C$_{15}$H$_{21}$NO$_2$.HCl.2/3 H$_2$O requires C, 60.9; H, 7.95; N, 4.7%.

EXAMPLE 16

(2R*,4aS*,8aR*)-Octahydro-8a-(3-methoxyphenyl)-2,4-dimethyl-2H-1,4-benzoxazine

The crude product of Example 10 (1.36 g) in dry ether (25 cm$^3$) was added dropwise to a stirred, refluxing suspension of lithium aluminium hydride (0.45 g) in dry ether (10 cm$^3$). The mixture was heated to reflux for 6 hr. and was then allowed to cool. Saturated Rochelle salt solution (50 cm$^3$) was added and the mixture was stirred to dissolve aluminium salts. The phases were separated and the aqueous phase was extracted with further ether. The extracts were dried (Na$_2$SO$_4$) and evaporated, leaving the title product as an oil (1.27 g). The crude title base (1.1 g) was converted in ethyl acetate to its hydrogen oxalate salt, which was recrystallised from ethyl acetate-methanol giving crystals (0.73 g), m.p. 213°-5° (decomp.).

Found: C, 62.3; H, 7.5; N, 3.6. C$_{17}$H$_{25}$NO$_2$.C$_2$H$_2$O$_4$ requires C, 62.45; H, 7.45; N, 3.8%.

EXAMPLE 17

(2R*,4aS*,8aR*)-3-(Octahydro-2,4-dimethyl-2H-1,4-benzoxazin-8a-yl)phenol

The oxalate salt from Example 16 (0.73 g) was slurried in dry toluene (7.5 cm$^3$) under nitrogen and treated with di-isobutylaluminium hydride (25% w/w in toluene 8 cm$^3$) at room temperature. The mixture was heated to reflux for 21 hr. then further di-isobutylaluminium hydride solution (4 cm$^3$) was added in 2 portions. Heating was continued for a further 28 hr, then the mixture was allowed to cool. The solution was treated with saturated Rochelle salt solution (50 cm$^3$), water (10 cm$^3$) and ether (20 cm$^3$) and stirred ½ hr. to dissolve the aluminium salts. The mixture was separated and the aqueous phase was extracted with ether. The combined organic phases were dried (Na$_2$SO$_4$) and evaporated, leaving crude title compound as a solid (0.59 g). The solid was converted to its hydrochloride in ethyl acetate-ether and the salt was recrystallised from ethyl acetate-methanol as colourless crystals (0.30 g, m.p. 291°-291.5° (decomp. before melting).

Found: C, 64.3; H, 8.2; N, 4.6. C$_{16}$H$_{23}$NO$_2$.HCl requires C, 64.5; H, 8.1, N, 4.7%.

EXAMPLE 18

(2R*,4aR*,8aS*)-2-Ethyl-octahydro-8a-(3-methoxyphenyl)-4-methyl-2H-1,4-benzoxazine A warm suspension of lithium aluminium hydride (0.8 g) in dry ether (20 cm$^3$) was stirred for 5 min. before the dropwise addition of the crude product of Example 11 (2.55 g) dissolved in ether (50 cm$^3$) over 15 min. The mixture was then heated to reflux for 6 hr. The cooled solution was treated with saturated Rochelle salt solution (75 cm$^3$) and water (25 cm$^3$) and stirred until the aluminium salts had dissolved. The phases were separated and the aqueous phase was extracted with ether. The combined organic solutions were dried (Na$_2$SO$_4$) and evaporated, leaving an oil (2.29 g).

The crude oil (2.07 g) in ethyl acetate was filtered into a warm solution of oxalic acid dihydrate (0.9 g) in ethyl acetate. The deposited crystals of the oxalate salt (1.74 g) were recrystallised from ethyl acetate-methanol to give pure title compound as the hydrogen oxalate (1.26 g), m.p. 207°-9° (decomp).

Found: C, 63.6; H, 7.8; N, 3.5. C$_{18}$H$_{27}$NO$_2$.C$_2$H$_2$O$_4$ requires C, 63.3; H, 7.7; N, 3.7%.

EXAMPLE 19

(2R*,4aR*,8aS*)-3-(2-Ethyl octahydro-4-methyl-2H-1,4-benzoxazin-8a-yl)phenol

The hydrogen oxalate product from Example 18 (1.09 g) was slurried in dry toluene (10 cm$^3$) under nitrogen and was treated with di-isobutylaluminium hydride (1.2 M in toluene, 14.4 cm$^3$, 17.3 mmol). The solution was heated to reflux under nitrogen for 22 hr. The cooled solution was treated with saturated Rochelle salt solution (50 cm$^3$), followed by ether (15 cm$^3$) and water (12.5 cm$^3$). The resulting suspension was stirred until the aluminium salts had dissolved, then the phases were separated and the aqueous phase was extracted with ether and chloroform. The combined organic phases were dried (Na$_2$SO$_4$) and evaporated, leaving the crude base as large prisms (0.9 g). The material was converted to its hydrochloride salt which was recrystallised from ethyl acetate-methanol giving the title compound hydrochloride as colourless crystals (0.56 g), m.p. 233°-5° (decomp).

Found: C, 65.4; H, 9.0; N, 4.15. C$_{17}$H$_{25}$NO$_2$.HCl requires C, 65.5; H, 8.4; N, 4.5%.

EXAMPLE 20

(2R*,4aS*,8aS*) and (2R*,4aR*,8aR*)-2-Ethylhexahydro-8a-(3-methoxyphenyl)-4-methyl-2H-1,4-benzoxazin-3(4H)-one The (1R*,2R*) product of Example 6 (4.7 g) in dichloromethane (50 cm$^3$) containing triethylamine (2.8 cm$^3$) was treated, with cooling, dropwise with 2-bromobutyrylchloride (2.5 cm$^3$). The solution was allowed to stand 1 hr. The solvent was removed and the residue was partitioned between ether (50 cm$^3$) and N hydrochloric acid (50 cm$^3$). The combined ether solutions were dried (Na$_2$SO$_4$) and evaporated, leaving the crude bromoamide as an oil (8.09 g).

The oily bromoamide (8.0 g) was treated in warm propan-2-ol (50 cm$^3$) with 10 N sodium hydroxide solution (4 cm$^3$) with vigorous stirring for 1 hr. The mixture was left overnight at room temperature and was then concentrated. The aqueous residue was diluted with water (50 cm$^3$) and the lactam product was extracted into ether, dried (Na$_2$SO$_4$) and evaporated, giving crude title compound as oil (6.02 g), containing a 60:40 mixture of isomers.

EXAMPLE 21

(2R*,4aR*,8aR*) and (2R*,4aS*,8aS*)-2-Ethyloctahydro-8a-(3-methoxyphenyl)-4-methyl-2H-1,4-benzoxazines A suspension of lithium aluminium hydride (1.9 g) in dry ether (50 cm$^3$) was heated to reflux for 5 min. before the slow addition of the mixed lactams products of Example 20 (6.02 g) in ether (100 cm$^3$) over ½ hr. The mixture was heated to reflux for 4 hr., cooled, treated with saturated Rochelle salt solution (100 cm$^3$) and water (25 cm$^3$), stirred until aluminium salts had dissolved, and separated. The aqueous phase was extracted with ether and the combined ether solutions were dried (Na$_2$SO$_4$) and evaporated, giving a mixture of title compounds as oil (5.04 g).

The mixture (4.9 g) was separated by chromatography over silica gel giving almost pure (2R*,4aR*,8aR*) isomer (2.27 g). The (2R*,4aS*,8aS*) isomer was obtained free from the (2R*,4aR*,8aR*) isomer but containing traces of other, minor impurities.

EXAMPLE 22

(2R*,4aR*,8aR*)-3-(2-Ethyloctahydro-4-methyl-2H-1,4-benzoxazin-8a-yl)phenol

Purified (2R*,4aR*,8aR*) isomer from Example 21 (99% pure by GLC) (2.04 g) in toluene (20 cm$^3$) was treated at room temperature under nitrogen with diisobutylaluminium hydride (25% w/w in toluene, 9.5 cm$^3$). The mixture was heated to reflux under nitrogen for 22 hr, cooled, treated with saturated Rochelle salt solution (50 cm$^3$) and ether (10 cm$^3$). The mixture was stirred to dissolve the aluminium salts, separated, and the aqueous phase was extracted with ether (3×50 cm$^3$). The combined organic phases were dried (Na$_2$SO$_4$) and evaporated, leaving crude title compound as a solid (1.85 g). The solid (1.77 g) was dissolved in ethyl acetate and added to a solution of oxalic acid dihydrate (0.81 g) in ethyl acetate. The solid deposited was recrystallised from ethyl acetate-methanol to give title compound hydrogen oxalate as needles (1.82 g), m.p. 186.5°–188° (decomp).

Found: C, 62.5; H, 7.55; N, 3.6. C$_{17}$H$_{25}$NO$_2$.C$_2$H$_2$O$_4$ requires C, 62.45; H, 7.45; N, 3.8%.

EXAMPLE 23

(2R*,4aS*,8aS*)-3-(2-Ethyloctahydro-4-methyl-2H-1,4-benzoxazin-8a-yl)phenol

Partially purified (2R*,4aS*,8aS*) product from Example 21 [87.8% 2R*,4aS*,8aS*; 4.5% 2R*,4aR*,8aR* by GLC] (1.48 g) in toluene (15 cm$^3$) was treated under nitrogen at room temperature with diisobutylaluminium hydride (25% w/w in toluene, 7 cm$^3$). The mixture was then heated to reflux for 17 hr, cooled, and treated with saturated Rochelle salt solution (50 cm$^3$) and water (10 cm$^3$). The mixture was stirred until the aluminium salts had dissolved and was separated. The aqueous phase was extracted with ether. The organic phases were dried (Na$_2$SO$_4$) and evaporated, giving crude title compound as an oil (1.46 g). The crude base (1.25 g) was dissolved in ethyl acetate and added to a solution of oxalic acid dihydrate (0.57 g) in ethyl acetate. The solid deposited was recrystallised from ethyl acetate-methanol giving the title compound as the hydrogen oxalate (1.07 g), m.p. 208°–210° (decomp).

Found: C, 62.6; H, 7.7; N, 3.6. C$_{17}$H$_{25}$NO$_2$.C$_2$H$_2$O$_4$ requires C, 62.45; H, 7.45; N, 3.8%.

EXAMPLE 24

(1R*,2S*)-1-(3-Methoxyphenyl)-2-methylamino-1-cyclopentanol

Crude 1-(3-methoxyphenyl)cyclopentene oxide (prepared according to the method of Ger. Offen. No. 2,942,644) is treated with ethanolic methylamine solution by the method of Example 1(b) above to give the title compound.

EXAMPLE 25

(1R*,2S*)-2-(2-bromopropion-N-methylamido)-1-(3-methoxyphenyl)-1-cyclopentanol

The product of Example 24 is treated with 2-bromopropionyl bromide by the procedure of Example 2 to give the crude title compound.

EXAMPLE 26

4a,6,7,7a-Tetrahydro-7a-(3-methoxyphenyl)-2,4-dimethyl-2H,5H-cyclopent[b][1,4]-oxazin-3(4H)-one Crude bromoamide product of Example 25 is treated with sodium hydroxide by the method of Example 3 to give the title compound.

EXAMPLE 27

Hexahydro-7a-(3-methoxyphenyl)-2,4-dimethyl-2H,5H-cyclopent[b][1,4]oxazine

The product of Example 26 is reduced by the procedure of Example 4a to give the title compound.

EXAMPLE 28

(1R*,2S*)-2-(2-Bromononan-N-methylamide)-1-(3-methoxyphenyl)-1-cyclohexanol

The product of Example 1 is treated with 2-bromononanoyl chloride by the method of Example 2 to provide the title compound.

EXAMPLE 29

Hexahydro-2-heptyl-8a-(3-methoxyphenyl)-4-methyl-2H-[1,4]-benzoxazin-3(4H)-one

The crude product of Example 28 is treated by the method of Example 2 to give the title product.

EXAMPLE 30

Octahydro-2-heptyl-8a-(3-methoxyphenyl)-4-methyl-2H-1,4-benzoxazine

The product of Example 29 is reduced by the procedure of Example 9a to give the title compound.

We claim:

1. A compound selected from the group consisting of a morpholine derivative of formula (I)

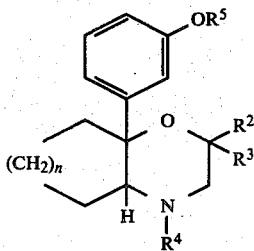

and a pharmaceutically acceptable acid addition salt thereof, wherein n represents 1,2 or 3, $R^2$ and $R^3$ are each hydrogen or alkyl of 1 to 10 carbon atoms, $R^4$ is hydrogen, lower alkyl, lower alkenyl, lower alkynyl, aryl(lower)alkyl, 2-tetrahydrofurylmethyl or cyclo(lower)alkylmethyl and $OR^5$ is hydroxy, acyloxy or lower alkoxy.

2. A compound as claimed in claim 1 wherein n is 2.

3. A compound as claimed in claim 1 which is octahydro-8a-(3-methoxyphenyl)-2,4-dimethyl-2H-1,4-benzoxazine or a pharmaceutically acceptable acid addition salt thereof.

4. A compound as claimed in claim 1 which is 3-(octahydro-2,4-dimethyl-2H-benzoxazin-8a-yl)phenol or a pharmaceutically acceptable acid addition salt thereof.

5. A compound as claimed in claim 1 which is 3-[(2R*,4aR*,8aS*)-octahydro-2,4-dimethyl-2H-benzoxazin-8a-yl]phenol or a pharmaceutically acceptable acid addition salt thereof.

6. A compound as claimed in claim 1 which is octahydro-8a-(3-methoxyphenyl)-4-methyl-2H-1,4-benzoxazine or a pharmaceutically acceptable acid addition salt thereof.

7. A compound as claimed in claim 1 which is 3-(octahydro-1-methyl-2H-1,4-benzoxazin-8a-yl)phenol or a pharmaceutically acceptable acid addition salt thereof.

8. A compound as claimed in claim 1 which is 2-ethyloctahydro-8a-(3-methoxyphenyl)-4-methyl-2H-1,4-benzoxazine or a pharmaceutically acceptable acid addition salt thereof.

9. A compound as claimed in claim 1 which is 3-(2-ethyloctahydro-4-methyl-2H-1,4-benzoxazin-8a-yl)phenol or a pharmaceutically acceptable acid addition salt thereof.

10. A pharmaceutical composition comprising a compound selected from the group consisting of a morpholine derivative of formula (I)

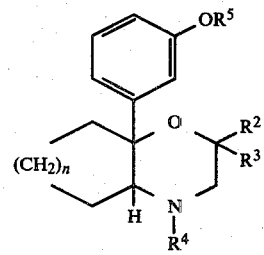

and a pharmaceutically acceptable acid addition salt thereof, wherein n represents 1,2 or 3, $R^2$ and $R^3$ are each hydrogen or alkyl of 1 to 10 carbon atoms, $R^4$ is hydrogen, lower alkyl, lower alkenyl, lower alkynyl, aryl(lower)alkyl, 2-tetrahydrofurylmethyl or cyclo(lower)alkylmethyl and $OR^5$ is hydroxy or acyloxy in association with a pharmaceutically acceptable carrier.

11. A method of treating a mammal in need of an analgesic or opiate antagonist which comprises administering to said mammal an analgesically or opiate antagonistically effective amount of a compound selected from the group consisting of a morpholine derivative of formula (I)

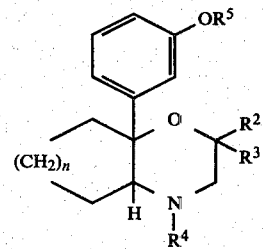

and a pharmaceutically acceptable acid addition salt thereof, wherein n represents 1, 2 or 3, $R^2$ and $R^3$ are each hydrogen or alkyl of 1 to 10 carbon atoms, $R^4$ is hydrogen, lower alkyl, lower alkenyl, lower alkynyl, aryl(lower)alkyl, 2-tetrahydrofurylmethyl or cyclo(lower)alkylmethyl and $OR^5$ is hydroxy or acyloxy.

* * * * *